(12) United States Patent
Kumar

(10) Patent No.: US 6,644,969 B2
(45) Date of Patent: Nov. 11, 2003

(54) SNAP-IN HEALING CAP AND INSERTION TOOL

(75) Inventor: Ajay Kumar, Palmdale, CA (US)

(73) Assignee: Nobel Biocare AB, Gothenburg (SE)

( * ) Notice: Subject to any disclaimer, the term of this patent is extended or adjusted under 35 U.S.C. 154(b) by 33 days.

(21) Appl. No.: 10/023,416

(22) Filed: Dec. 17, 2001

(65) Prior Publication Data

US 2002/0110784 A1 Aug. 15, 2002

Related U.S. Application Data

(63) Continuation-in-part of application No. 09/662,106, filed on Sep. 14, 2000, now Pat. No. 6,394,806.
(60) Provisional application No. 60/153,843, filed on Sep. 14, 1999.

(51) Int. Cl.[7] .............................. A61C 8/00; A61C 3/00
(52) U.S. Cl. ........................................ 433/173; 433/141
(58) Field of Search .................................. 433/141, 172, 433/173, 174, 177

(56) References Cited

U.S. PATENT DOCUMENTS

| | | | |
|---|---|---|---|
| 4,836,781 A | 6/1989 | Meinershagen | 433/141 |
| 4,856,994 A | 8/1989 | Lazzara et al. | 433/173 |
| 5,195,891 A | 3/1993 | Sulc | 433/173 |
| 5,417,570 A | 5/1995 | Zuest et al. | 433/177 |
| 5,492,471 A | 2/1996 | Singer | 433/172 |
| 5,904,483 A | 5/1999 | Wade | 433/173 |
| 6,206,696 B1 | 3/2001 | Day | 433/141 |

*Primary Examiner*—Cary E. O'Connor
(74) *Attorney, Agent, or Firm*—Knobbe, Martens & Olson, Bear, LLP.

(57) ABSTRACT

A healing cap is provided for covering of an implant installed in a patient's mouth. The healing cap comprises a proximal end and a distal end. The proximal end is adapted to be inserted within a coronal opening formed in the implant. The healing cap further includes resilient fingers for engaging corresponding surfaces formed within the coronal opening of the implant. The distal end of the healing cap can include an indentation for receiving a snapping portion of an insertion tool.

27 Claims, 9 Drawing Sheets

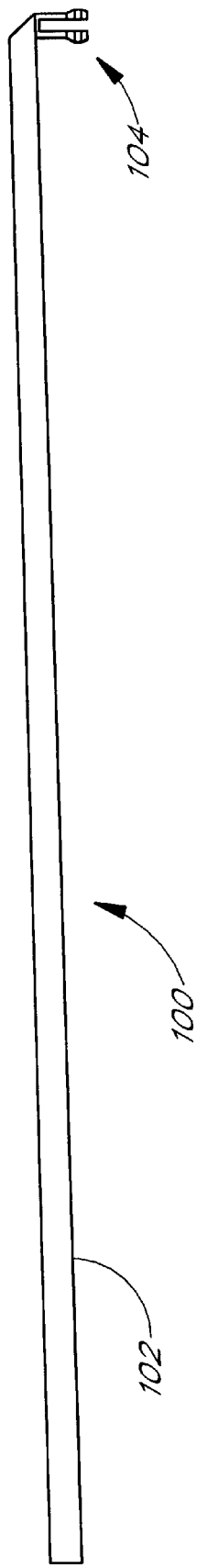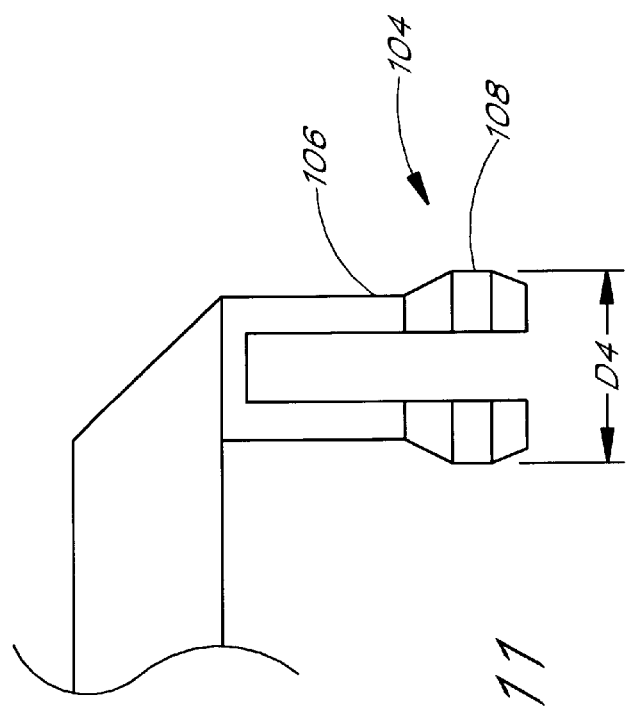

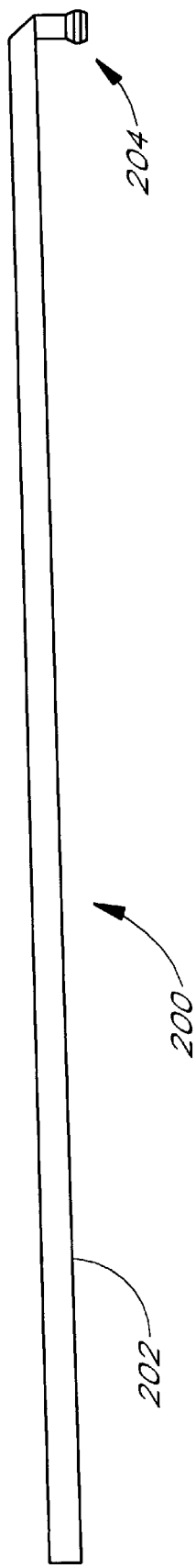
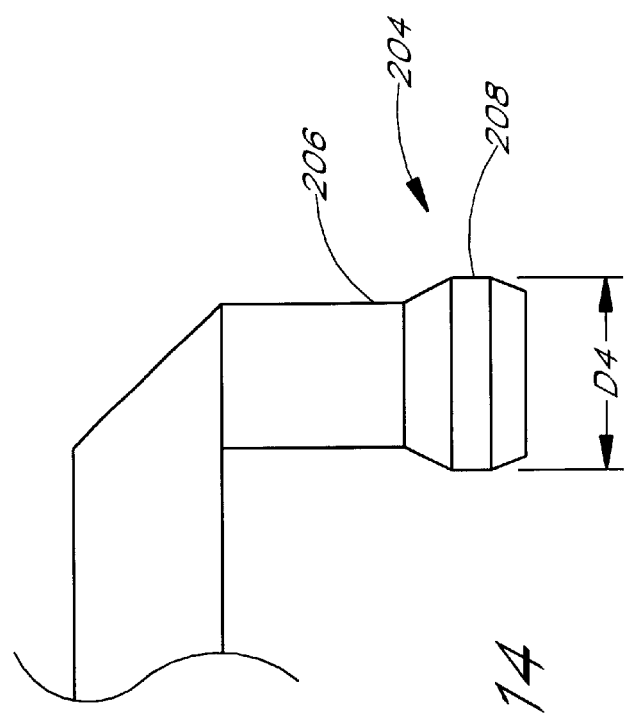
FIG. 13
FIG. 14

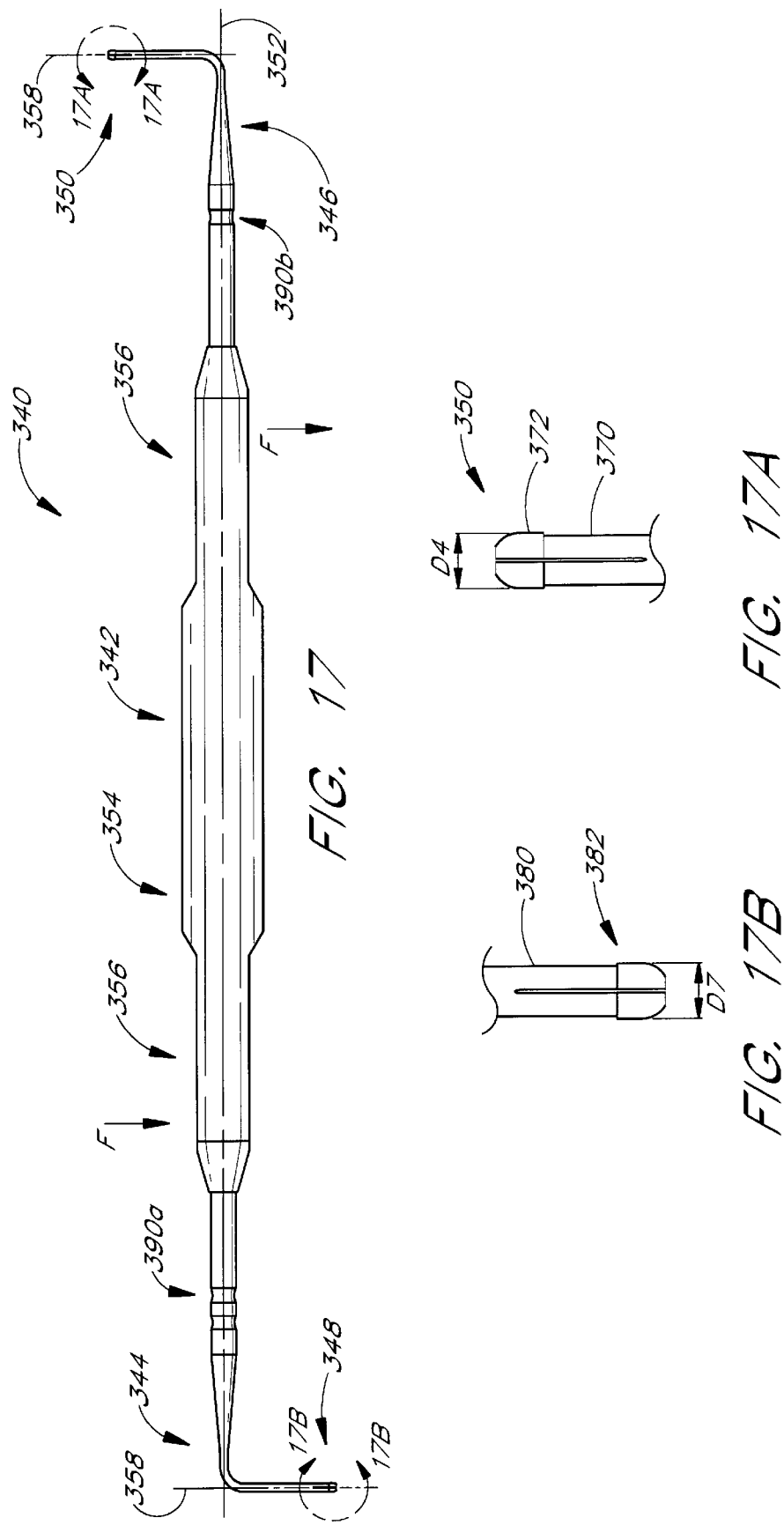

SNAP-IN HEALING CAP AND INSERTION TOOL

PRIORITY INFORMATION

The present application is a continuation-in-part of U.S. patent application Ser. No. 09/662,106, filed Sep. 14, 2000, now U.S. Pat. No. 6,394,806, which claims priority and benefit under 35 U.S.C. §119(e) of U.S. Provisional Patent Application Serial No. 60/153,843, filed Sep. 14, 1999.

BACKGROUND OF THE INVENTION

1. Field of the Invention

This invention relates to methods and devices that are used in implant dentistry to replace a natural tooth with a prosthetic tooth. More particularly, the invention relates to an improved healing cap that covers a dental implant after stage one surgery and an insertion tool that can be used to insert and/or remove the healing cap.

2. Description of the Related Art

Implant dentistry involves the restoration of edentulous area(s) in a patient's mouth using artificial components, including typically an implant fixture or root and a prosthetic tooth and/or final abutment which is secured to the implant fixture. According to state of the art techniques, the process for restoring a tooth and its root is carried out generally in three stages.

Stage I involves implanting the dental implant fixture into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant fixture to be implanted. Then, the dental implant fixture is inserted into the hole in the jawbone, typically by screwing, although other techniques are known for introducing the implant in the jawbone.

The implant fixture itself is typically fabricated from commercially pure titanium or a titanium alloy. Such materials are known to produce osseointegration of the fixture with the patient's jawbone. The dental implant fixture also typically includes a hollow threaded bore through at least a portion of its body and extending out through its proximal end which is exposed through the crestal bone for receiving and supporting the final tooth prosthesis and/or various intermediate components or attachments.

After the implant is initially installed in the jawbone a temporary healing screw or healing cap, which is ordinarily made of a dental grade metal, is secured over the exposed proximal end in order to seal the internal bore. The healing screw typically includes a threaded end, which is screwed into the internal bore of the implant. After the healing screw is in place, the surgeon sutures the gum over the implant to allow the implant site to heal and to allow desired osseointegration to occur. Complete osseointegration typically takes anywhere from four to ten months.

During stage II, the surgeon re-accesses the implant fixture by making an incision through the patient's gum tissues. The healing screw is then removed, exposing the proximal end of the implant. A mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site.

Stage III involves fabrication and placement of a cosmetic tooth prosthesis to the implant fixture. The plaster analogue provides laboratory technicians with a model of the patient's mouth, including the orientation of the implant fixture relative to the surrounding teeth. Based on this model, the technician constructs a final restoration. The final step in the restorative process is replacing the temporary healing abutment with the final restoration.

There are several recurring problems or difficulties associated with securing the healing screw or cap to the implant during stage one and with removing the healing screw or cap during stage two surgery. For example, screwing the healing screw into the implant during stage one is time consuming, difficult and requires a secondary tool such as a screwdriver. Moreover, because the healing screw is small, it is difficult to handle and may be accidentally dropped into the patient's mouth if adequate care is not taken. Unscrewing the healing screw from the implant during stage two also is time consuming, difficult and requires an additional tool such as a screwdriver. Furthermore, the healing screw also may be accidentally dropped into the patient's mouth as it is removed from the implant if adequate care is not taken.

It should be appreciated that a set of two or more teeth can be replaced using the same procedure outlined above. In such a case, a single implant supports two or more prosthetic teeth. The present invention applies equally to the replacement of one tooth or multiple teeth.

SUMMARY OF THE INVENTION

It is an objective of this invention to provide an improved dental implant and healing cap that enables a surgeon to quickly and simply attach the healing cap to the dental implant without the need for an additional tool. It is another object of this invention to provide a healing cap that is quickly and simply removed from the implant. It is yet another object of the invention to provide a healing cap made of an inexpensive injection-molded plastic or any of a variety of bio-compatible materials, such as, for example, titanium, stainless steel, ceramic, or any combination thereof.

In one embodiment, the present invention provides a combination comprising a dental implant, a healing cap for covering a top surface of the implant and a tool for inserting the healing cap. The dental implant has a coronal opening. The healing cap comprises a proximal end and a distal end. The proximal end is configured with one or more prongs adapted to be inserted into the coronal opening of the implant and to engage and secure the healing cap to the implant. The one or more prongs of the proximal end are adapted such that a healing cap removal force is required to disengage the healing cap from the dental implant. The distal end of the healing cap includes an indentation having a neck with a diameter smaller than a diameter of an adjacent portion of the indentation. The insertion tool comprises a first portion with one or more prongs adapted to be inserted into the indentation. The first portion is adapted such that a first removal force is required to remove the one or more prongs of the first portion from the indentation. The first removal force is less than the healing cap removal force.

In another embodiment, the present invention provides a set of dental components comprising a dental implant, a healing cap for covering a top surface of the dental implant when installed in a patient's jawbone and an insertion tool. The healing cap comprises a first end adapted to be snappingly mated to the implant with a healing cap removal force. The healing cap also includes a second end adapted to completely cover the top surface of the implant. The insertion tool includes a first portion to be snappingly mated to the second end of the healing cap with a first removal force. The first removal force is less than the healing cap removal force.

In yet another embodiment, the present invention provides a method of installing and removing a healing cap that covers a top surface of an implant installed in a patient's jawbone. The method comprises, in sequence, engaging in a snap fit a first portion of an insertion tool with a top portion of the healing cap, positioning the healing cap over a dental implant, inserting a proximal end of the healing cap into a coronal opening of the implant until the proximal end engages the coronal opening in a snap fit so as to secure the healing cap to the implant, and separating the first portion of the insertion tool from the top portion of the healing cap.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments and obvious variations thereof are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of the invention will now be described with reference to the drawings of the preferred embodiments, which are intended to illustrate and not to limit the invention, and in which:

FIG. 10 is a side elevational view of an insertion tool having certain features and advantages according to the present invention;

FIG. 11 is a close up view of the snapping portion of the insertion tool of FIG. 10;

FIG. 13 is a modified arrangement of a removal tool having certain features and advantages according to the present invention;

FIG. 14 is a close up view of the snapping portion of the removal tool of FIG. 13;

FIG. 17 is a side view of another modified embodiment of an insertion tool that has certain features and advantages according to the present invention.

FIG. 17A is a close up view of a portion of FIG. 17 labeled 17A.

FIG. 17B is a close up view of a portion of FIG. 17 labeled 17B.

DETAILED DESCRIPTION OF THE PREFERRED EMBODIMENT

Figure 3:
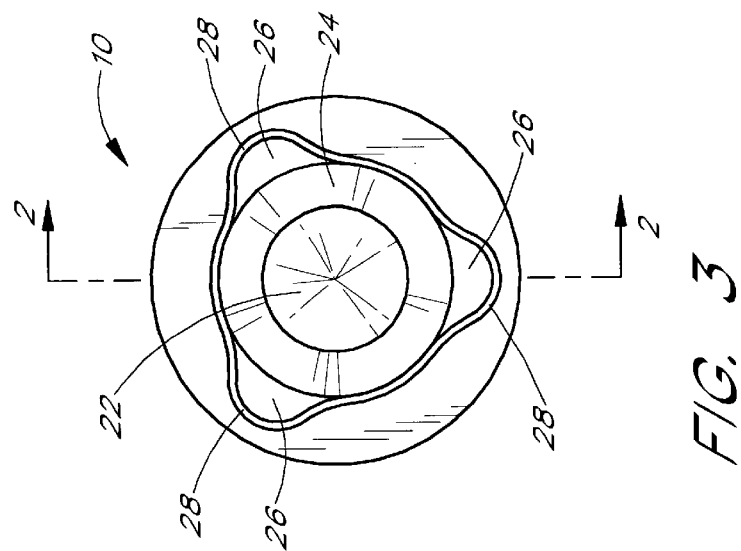
FIG. 3 is a top view of the dental implant of FIG. 1.
Figure 1:
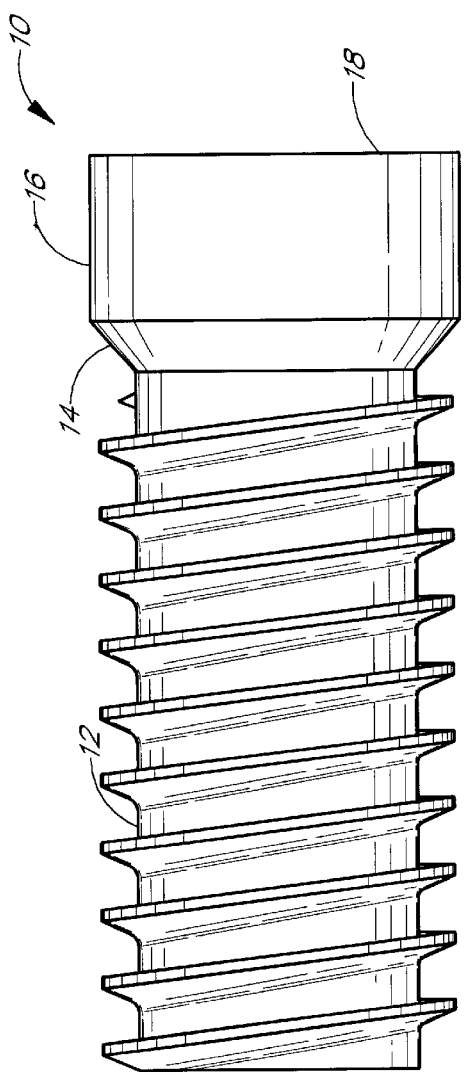
FIG. 1 is a side view of a dental implant having certain features and advantages according to the present invention.
Figure 2:
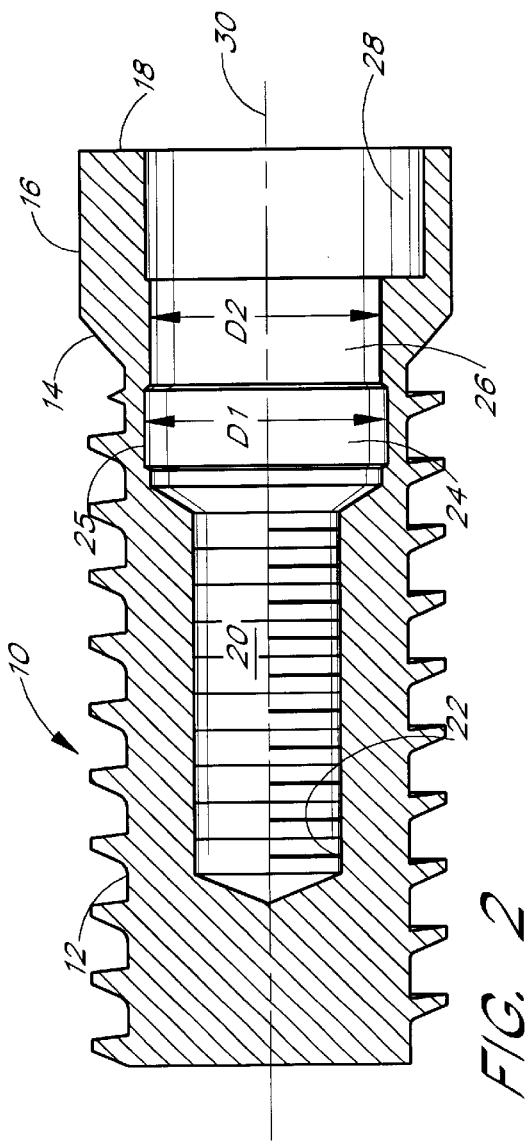
FIG. 2 is a cross-sectional view of the dental implant of FIG. 1 taken along line 2—2 of FIG. 3.
Figure 4:
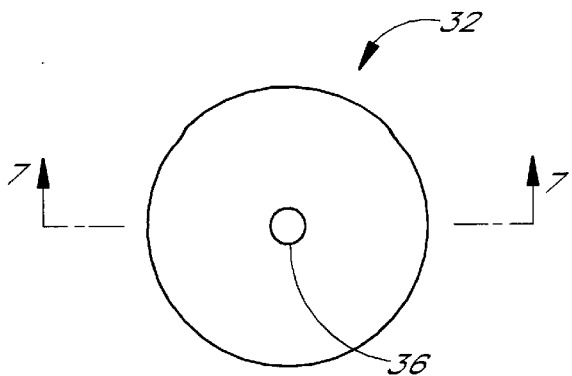
FIG. 4 is a top view of a healing cap having certain features and advantages according to the present invention.

FIGS. 1–3 illustrate a dental implant 10 particularly suited for receiving a snap-in healing cap having certain features and advantages according to one embodiment of the present invention. The implant 10 has an outer surface that is preferably divided into three regions: a body portion 12, a neck region 14, and a top portion 16. The body portion 12 preferably includes threads, and represents the portion of the implant 10 that is placed in either the mandible or the maxilla. As shown, the body portion 12 of the implant is substantially cylindrical; however, the body portion 12 could also assume a tapered or other known implant shapes, as desired. The threads of the body portion 12 preferably match preformed threads formed along the inner surface of an osteotomy formed in the patient's jawbone. However, the implant 10 could also be designed to be self-tapping. Preferably, the top portion 16 of the implant is substantially cylindrical and has a top surface 18 that is substantially flat.

As best seen in FIGS. 2 and 3, the implant 10 includes an inner cavity 20. The inner cavity 20 preferably includes a screw chamber 22, a snapping chamber 24, and an indexing chamber 26. Preferably, the diameter of the screw chamber 22 is smaller than the diameter of the snapping chamber 24. The snapping chamber 24 preferably includes a recess 25 that has an inner diameter D1 that is slightly larger than the diameter D2 of at least the adjacent portion of the indexing chamber 26.

The screw chamber 22 is preferably sized and configured so as to receive a bolt (not shown). The bolt can be used to temporarily or permanently attach a dental component, such as, for example, a temporary healing abutment or a final restoration to the implant 10. As will be described later, the snapping chamber 24 and the recess 25 are sized and configured to engage a corresponding snapping structure in a healing cap.

The indexing chamber 26 is best seen in FIGS. 2 and 3. In the illustrated arrangement, the indexing chamber 26 is substantially cylindrical with three lobes 28 that extend from the top surface 18 to the bottom of the indexing portion 26.

The three lobes 28 are preferably substantially half circular in shape and are symmetrically situated around the perimeter of the indexing portion 26. Preferably, the center of each lobe 28 is about 120° apart from each other relative to a center axis 30 of the implant 10.

It should be appreciated that the indexing chamber 26 can be formed into a wide variety of other suitable shapes that may be used with efficacy, giving due consideration to the goals of providing anti-rotation of mating components. For example, the anti-rotation chamber 26 could comprise one or more radially inwardly or outwardly extending splines or recesses, flats, polygonal configurations and other anti-rotation complementary surface structures. In addition, an anti-rotational structure such as a hexagonal recess or protrusion may be situated on the top surface 18 of the implant 10. Nevertheless, the illustrated arrangement appears to provide clinical efficacy, ease of use and also minimizes stress concentrations within the anti-rotation chamber 26.

FIGS. 4–7 illustrate one embodiment of a healing cap 32 having features and advantages in accordance with the present invention. The healing cap 32 is made of any of a variety of bio-compatible materials, such as, for example, an injection molded dental grade plastic, titanium, stainless steel, ceramics, and any combination thereof. Preferably, the healing cap 32 is made of an inexpensive injection molded dental grade plastic because such a material is generally less expensive than metal and ceramic materials.

Figure 5:
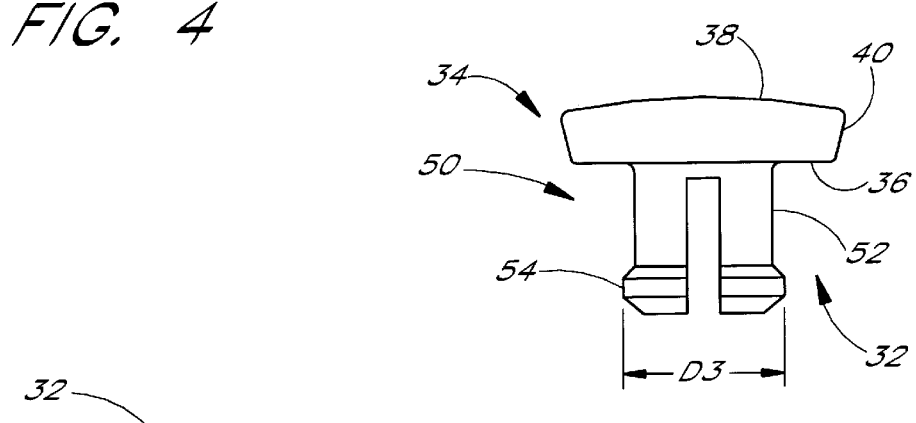
FIG. 5 is a side elevational view of the healing cap of FIG. 4.
Figure 6:
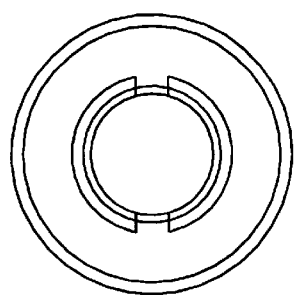
FIG. 6 is a bottom view of the healing cap of FIG. 4.
Figure 7:
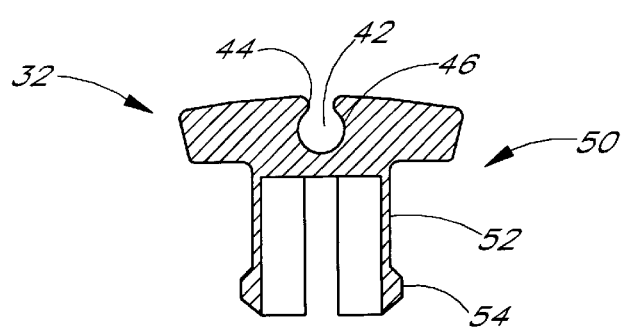
FIG. 7 is a cross-sectional view of the healing cap of FIG. 4 taken along line 7—7 of FIG. 4.

As best shown in FIGS. 5 and 7, the healing cap 32 has two main parts: a cover portion 34 and a snapping portion 50. The cover portion 34 has a substantially flat lower surface 36 or a non-planar surface with is complementary to the top surface 18 of the implant 10. The diameter of the lower surface 36 is approximately the same as the top surface 18 of the implant 10. The cover portion 34 also includes a top surface 38 that is substantially smooth and in the illustrated arrangement has a diameter slightly larger than the lower surface 36. In the illustrated arrangement, a side wall 40 connects the top surface 38 to the lower surface 36.

Preferably, the cover portion 34 also includes at least one indentation 42 which is desirably located near or at the center of the top surface 38. The indentation 42 includes a neck 44, which has a diameter that is smaller than a diameter of a lower portion 46 of the indentation 42. The function of the indentation 42 will be described in detail below.

The illustrated snapping portion 50 consists of a plurality of lever arms, prongs or tangs 52. Each lever arm 52 preferably includes a protrusion 54. The protrusions 54 are preferably sized and configured to snap into and resiliently engage the snapping chamber 24 of the implant 10. Accordingly, the protrusions 54 have an outer diameter D3 that is preferably slightly larger than the inner diameter D2 of the indexing chamber 26 (see FIG. 2). Although in the illustrated arrangement the protrusions 54 are beveled (i.e., comprising two slanted sides and one flat side), it should be appreciated that the protrusions can also be fully or partially rounded as desired.

Although two lever arms 50 with protrusions 54 thereon are illustrated, this number may be varied to produce the desired retention force and simplify manufacturing. For example, as few as one protrusions may be sufficient, particularly in an interference fit construction such as that achieved with the structure shown in FIG. 2, where the protrusion 54 snap fits into a radially outwardly extending recess within the implant 10. Six or more may alternatively be used.

Figure 8A:
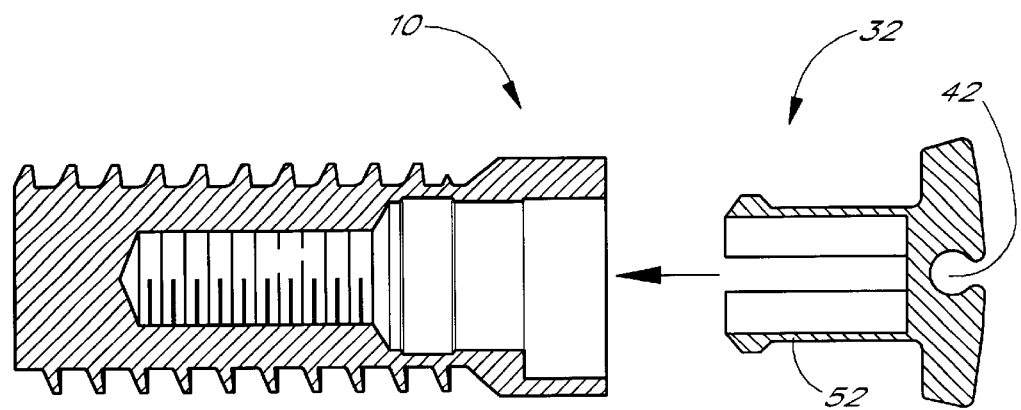
FIGS. 8A–C are partial cross-sectional time assembly views illustrating the healing cap of FIG. 4 being inserted into the implant.
Figure 8B:
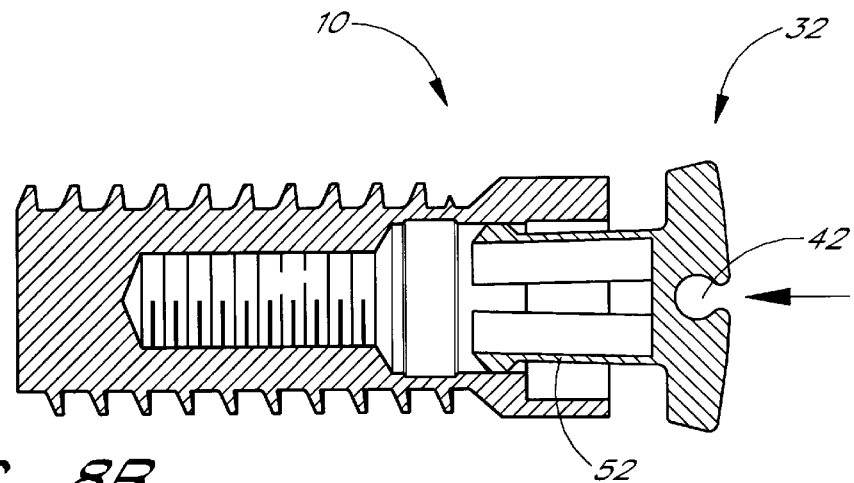
Figure 8C:
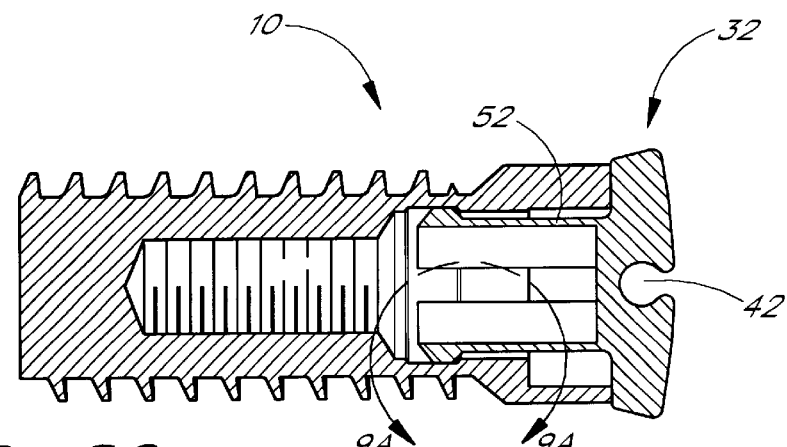
Figure 9A:
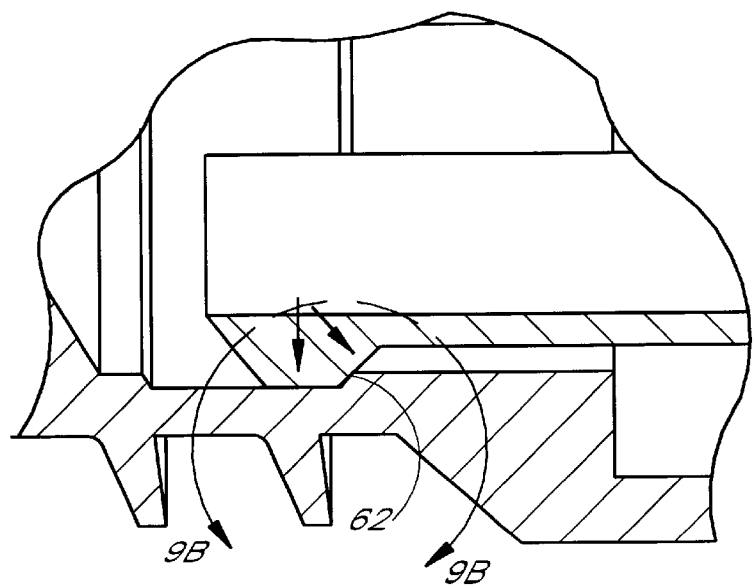
FIGS. 9A and B are detail views of the healing cap in the snapping chamber of implant assembly.
Figure 9B:
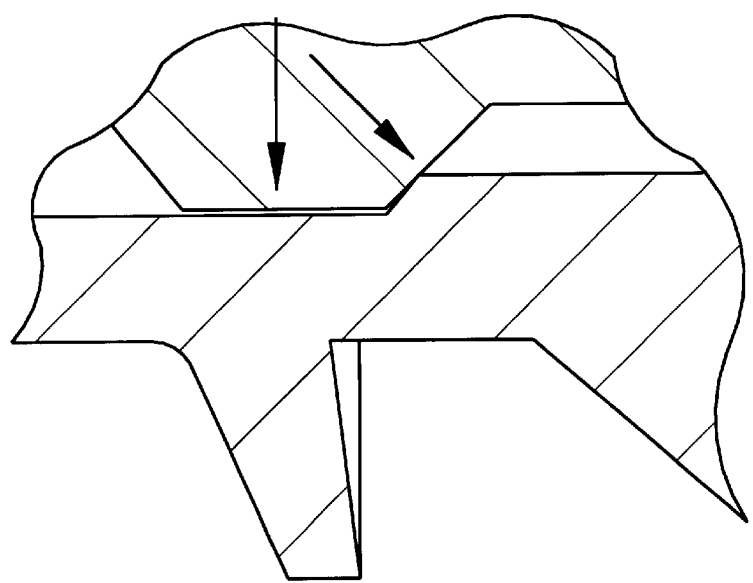

Referring to FIGS. 8A–C, to attach the healing cap 32 to the implant 10 during stage I, the surgeon simply places healing cap 32 over the implant 10 and pushes the snapping portion 50 of the healing cap 32 into the implant 10, as will be described in more detail below. As mentioned above, the protrusions 54 of the healing cap 32 preferably have at least a slightly larger diameter D3 than the inner diameter D2 of the indexing chamber 26. Accordingly, the snapping portion 50 of the healing cap 32 is compressed as it passes through the indexing chamber 26 (see FIGS. 8A and B). Once the prongs 52 reach the snapping chamber 24, they partially expand forming a snap fit between the healing cap 32 and the implant 10 (see FIG. 8C). Additionally and advantageously, as the healing cap 32 is mated against the top surface 18 of the implant 10, the prongs 52 preferably resiliently engage a slanted inner surface 62 of the snapping chamber 22 (see FIG. 9A). Thus, the pressure exerted against the partially compressed prongs 52 by the slanted inner surface 62 of the snapping chamber 22 creates a responsive downward pulling force. This downward pulling force on the cap 32 causes the lower surface 36 of the healing cap 32 and the top surface 18 of the implant 10 to form a seal (see FIG. 8C). Advantageously, this prevents and/or minimizes leakage of saliva and bacterial contaminants into the implant 10 and thus reduces the risk of infection between stage 1 surgery and stage II surgery.

Clinically and advantageously, the dentist can be assured of the proper placement or seating of the healing cap 32 because as the healing cap 32 is pulled or urged down into the implant 10 the dentist can "feel" the snap fit and hear the audible "click" as the prongs 52 snap into the snapping chamber 24 of the implant 10. Additionally, the dentist may visually confirm that the healing cap 32 is properly placed or seated by viewing the lower surface 36 of the healing cap 32 and the top surface 18 of the implant 10 using a dental mirror. If desired, the proper placement or engagement of the healing cap 32 may be confirmed by attempting to remove the healing cap 32. A properly seated coping will have perceivable resistance to removal forces as the prongs 52 become compressed as they are pulled back into the indexing chamber 26 (see FIG. 8B).

To remove the healing cap 32 during stage two, the surgeon may use a removal tool 100, which is depicted in FIGS. 10 and 11. The tool 100 preferably includes a proximal stem 102 and a distal snapping portion 104. The distal snapping portion 104 is similar in shape and function as the snapping portion 50 of the healing cap 32. The main difference is that the snapping portion 104 of the removal tool 100 is configured to engage the indentation 42 on top of the healing cap 32 (FIG. 7) in a snap fit. Accordingly, the snapping portion 104 includes a plurality of prongs, tangs or lever arms 106. Each lever arm 106 preferably includes a protrusion 108 that can be beveled (as illustrated) or rounded. As mentioned above, the protrusions 108 are preferably sized and configured to snap into and resiliently engage the indentation 42 of the healing cap 10 (see FIG. 7). Accordingly, the protrusions have an outer diameter D4 that is slightly larger than the diameter of the neck 44 of the indentation 42. Although two lever arms 106 with protrusions 108 thereon are illustrated, this number may be varied to produce the desired retention force and simplify manufacturing. For example, as few as one protrusions may be sufficient or six or more may alternatively be used.

Figure 12A:
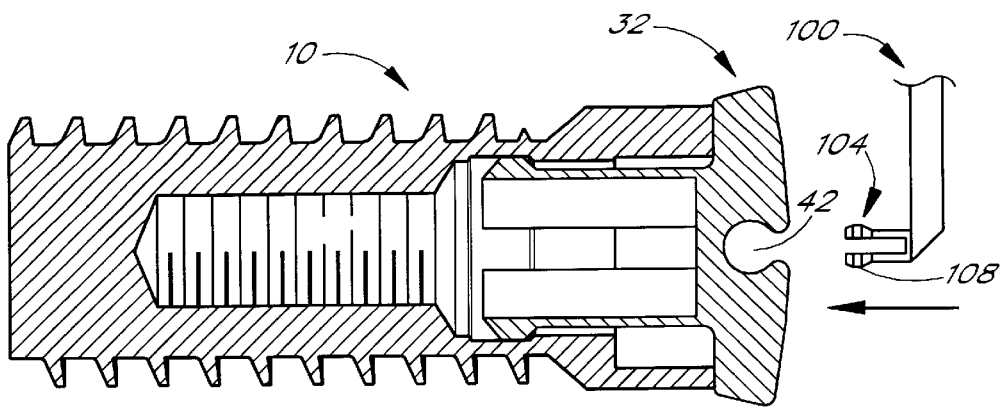
FIGS. 12A–C are partial cross-sectional time assembly views illustrating the removal tool of FIG. 10 being inserted into the healing cap of FIG. 4, which is already inserted into the implant of FIG. 1.
Figure 12B:
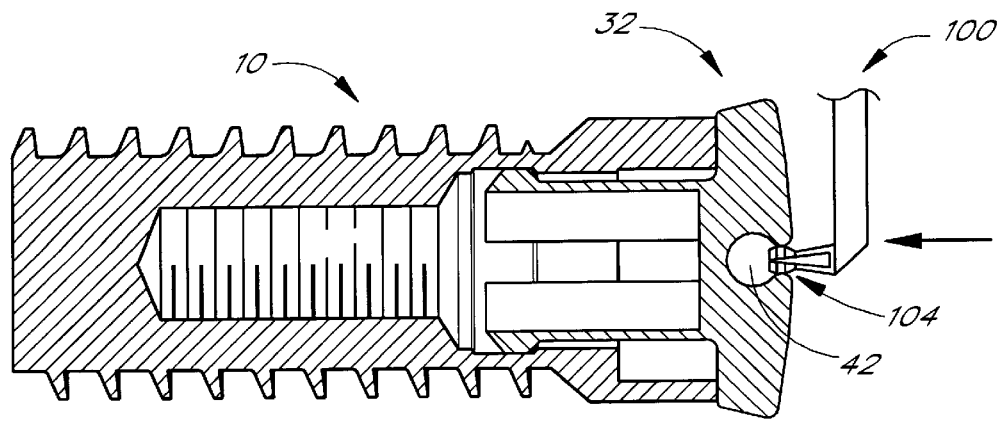
Figure 12C:
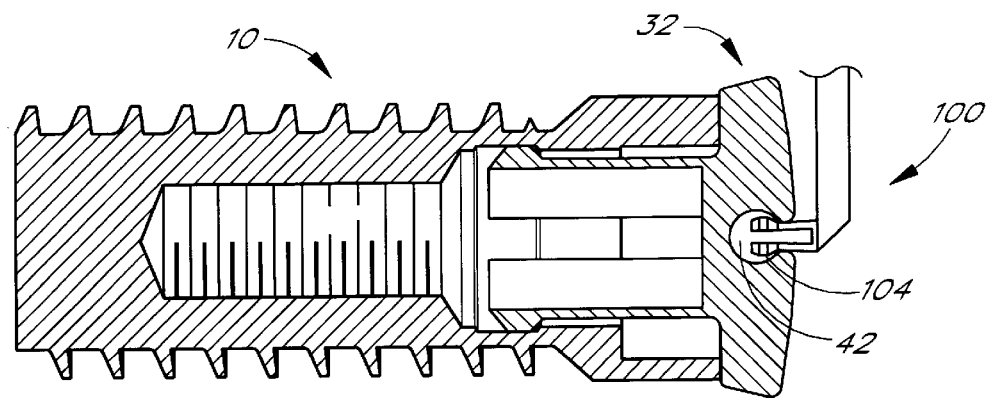

Referring to FIGS. 12A–B, to remove the healing cap 32 from the implant 10 during stage II, the dentist simply places the snapping portion 104 of the removal tool 100 over the indentation 42 and pushes the snapping portion 104 into the indentation 42. As mentioned above, the protrusions 108 of the handle 100 preferably have at least a slightly larger diameter D4 than the neck 44 of the indentation 42. Accordingly, the snapping portion 104 of the handle 100 is compressed as it passes through the neck 44 (see FIG. 12B). Once the protrusions 108 reach the lower portion 46 of the indentation 42, the prongs 106 partially expand forming a snap fit between the handle 100 and the healing cap 32.

The handle 100 and healing cap 32 are preferably configured so that a force required to remove the healing cap 32 from the implant 10 is less than the force required to remove the handle 100 from the healing cap 32. Therefore, when the dentist lifts the removal tool 100 away from the implant 10, the healing cap 32 remains attached to the handle 100 but detaches from the implant 10.

The snapping forces between the healing cap 32, and the implant 10 are determined primarily by the outer diameter of the protrusions 54, the inner diameter of the recess 25, the inner diameter of the indexing chamber 26, and relationships, such as, the friction or interference fit between contacting mated surfaces. Similarly, the snapping forces between the handle 100 and the healing cap 32 are determined primarily by the outer diameter D4 of the protrusions 108, the inner diameter of the lower portion 46, the inner diameter of the neck 44, the friction or interference fit between contacting mating surfaces. To decrease the snapping force, the inner diameter of the protrusions 54, 108 can also be decreased while maintaining the inner diameters of the recess 25 and the indexing chamber 26 and the inner diameters of the lower portion 46 and neck 44. The snapping force may also be decreased or controlled by increasing the diameter of the indexing chamber 26 (or the neck 44) while maintaining the size of the protrusions 43 (or 108) and the recess 25 (or lower portion 46). In addition, the length and cross-section of the lever arms 106 as well as construction material may be varied to vary the retention force.

As mentioned above, the healing cap can be made from any of a variety of bio-compatible materials, such as, for example, dental grade plastic, titanium, stainless steel, ceramic, or any combination thereof. The healing cap 32 is preferably made of an injection molded dental grade plastic, which is particularly useful for forming the snapping portion 52 because of its resilient properties. Accordingly, in one arrangement of the present invention, the cover 34 of the healing cap 32 is made of a metal or ceramic material while the snapping portion 50 is made a plastic material.

If the healing cap 32 and/or the handle 100 and/or parts thereof are made of metal, such as, for example, Titanium or Stainless Steel, the surface of the protrusions 54, 108 may preferably be coated or otherwise treated with Teflon, diamond-like carbon coating (e.g. amorphous diamond), or titanium anodic coating, or any other lubricious coating capable of making the surfaces slide easier. See, for example, U.S. Pat. No. 5,833,463 incorporated herein by reference.

FIGS. 13 and 14 illustrate a modified arrangement of a removal tool 200. As with the previous arrangement, the removal tool 200 includes a proximal handle 202 and a distal snapping portion 204. The snapping portion 204 includes a prong 206 and a protrusion 208, which has a diameter D4 greater than the diameter of the neck 44 of the healing cap 32. The main difference in this arrangement is that the snapping portion 204 is not resilient. Thus, to remove the healing cap 32 during stage II, the dentist places the snapping portion 204 of the removal tool 200 over the indentation 42 and pushes the snapping portion 204 into the indentation 42. As mentioned above, the protrusions 208 of the handle 200 preferably, have at least a slightly larger diameter D4 than the neck 44 of the indentation 42. Accordingly, the neck 44 is configured to deflect as the protrusion 208 passes through the neck 44. Once the protrusion 208 reach the lower portion 46 of the indentation 42, the neck 44 return to its original position thereby forming a snap fit between the handle 200 and the healing cap 32. In such an arrangement, the healing cap 32 is preferably made of plastic so that the neck is resilient.

It should also be noted that although in the illustrated embodiments the healing cap 32 is removed from the implant 10 by engaging a removal tool with the healing cap 32, the healing cap 32 can also be separated from the implant 10 by using a dental pick (not shown) or other conventional dental implement. Specifically, the dentist can use the dental pick or other implement to pry the healing cap 32 away from the implant 10. In such an arrangement, the healing cap 32 does not necessarily include the indentation 42.

Figures 15, 16:
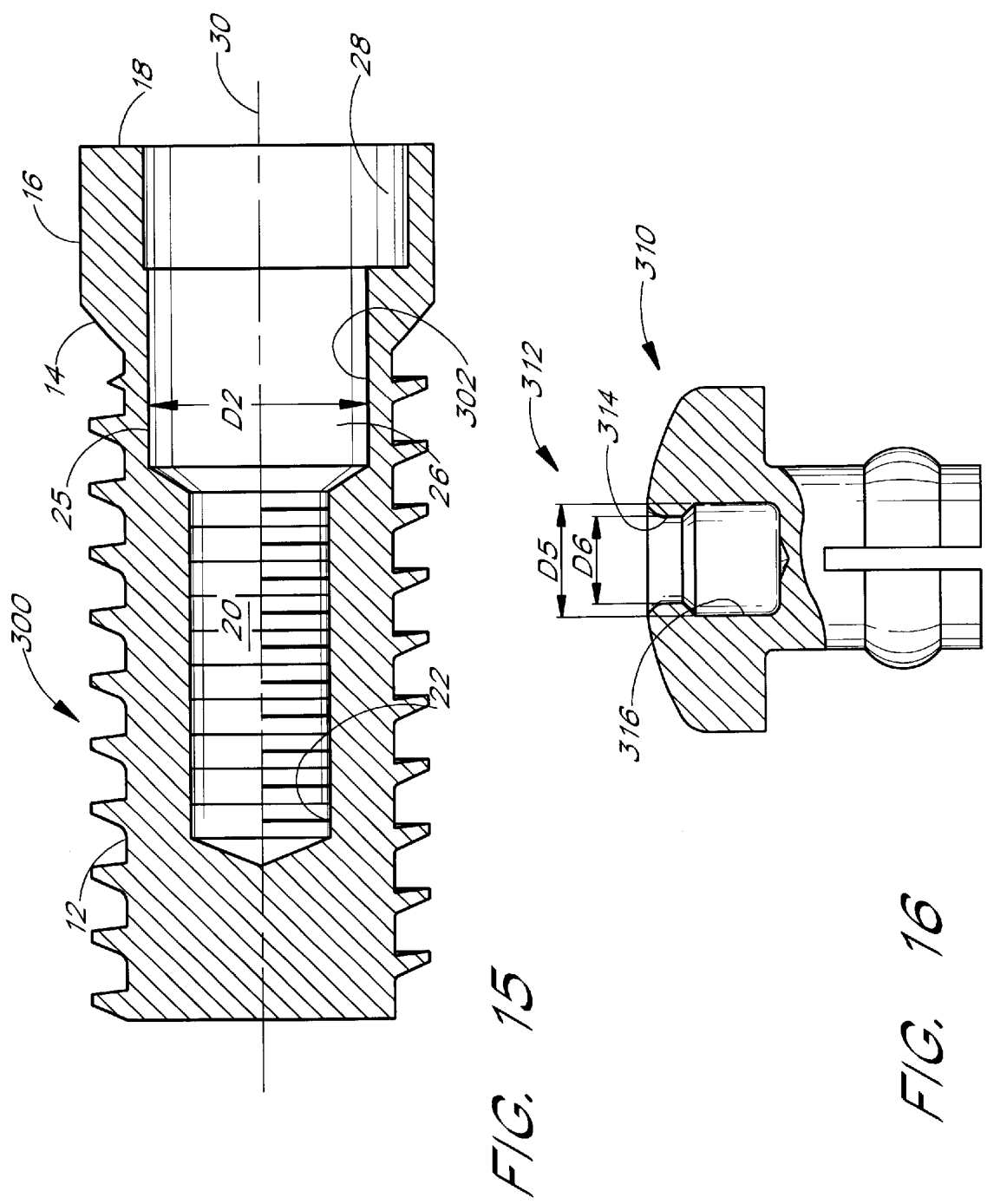
FIG. 15 is a cross-sectional view of a modified dental implant having certain features and advantages according to the present invention.
FIG. 16 is a partial cross-sectional view of a modified embodiment of a healing cap having certain features and advantages according to the present invention.

FIG. 15 illustrates a modified dental implant 300, which can also be used with the snap-in healing cap 32 described above. Like numbers are used to refer to parts similar to those of FIGS. 1–3. In this embodiment, the inner cavity 20 of the dental implant 300 does not include a snapping chamber. As such, the indexing chamber 26 extends to the screw chamber 22.

In the illustrated embodiment, when the healing cap 32 is engaged with the dental implant 300, the prongs 52 and the protrusions 54 of the healing cap 32 are configured contact the walls 302 of the indexing chamber 26 and exert a positive force outwardly in a radial direction. Accordingly, the protrusions 54 (see FIG. 5) have an outer diameter D3 that is preferably slightly larger than the inner diameter D2 of a portion of the indexing chamber 26. As such, the healing cap 32 is secured to the top surface 18 of the dental implant 10 by the friction or interference fit between the protrusions 54 and the walls 302 of the implant 300.

FIG. 16 illustrates a modified embodiment of a healing cap 310, which can be used with the dental implants of FIGS. 1–3 and FIG. 15. Like numbers are used to refer to parts similar to those of FIGS. 4–7. In this embodiment, the indentation 312 comprises a neck 314 and a cylindrical portion 316, which lies beneath the neck 314. The neck 314, at its smallest point, has a diameter D5, which is smaller than the smallest diameter D6 of the cylindrical portion 316. In one embodiment, the neck has a diameter D5 of approximately 0.065 inches while the cylindrical portion has a diameter of approximately 0.080 inches.

FIG. 17 illustrates an insertion tool 340, which has certain features and advantages according to the present invention. In the illustrated embodiment, the tool 340 comprises a first section 344 and a second section 346 that are preferably connected by a common handle 342. In a modified embodiment, the first and second sections 344 and 346 can be connected to separate handles. The first section 344 includes an insertion snapping portion 348 while the second section 346 includes a removal snapping portion 350.

In the illustrated embodiment, the insertion and removal snapping portions 348, 350 extend in opposite directions with respect to a longitudinal axis 352 of the handle. However, in modified embodiments, the insertion and removal snapping portions 348, 350 can extend in the same direction or be rotated less than 180 degrees from each other.

In the illustrated embodiment, the handle 342 comprises a substantially cylindrical section 354 having a first diameter which tapers down to a smaller second diameter at the first and second sections 344, 346. The substantially cylindrical section 354 has preferably has a diameter of at least approximately 0.5 inches, such that the handle 354 can be easily grasped by the dental practitioner. The substantially cylindrical section preferably includes a pair of flattened portions 356 near the first and second ends 344, 346. The flattened portions 356 preferably define a plane, which lies generally traverse and more preferably perpendicular to an axis 358 extending through the nearest snapping portion 348, 350. As such, the flattened portions 356 provide an ergonomic surface to which a force F can be applied to insert and remove the snapping portions 348, 350 as will be explained in more detail below.

The removal snapping portion 350 is similar in shape and function as the snapping portion 104 of the removal tool 100 described above. That is, the removal snapping portion 350 is configured to engage the indentation 42 on top of the healing cap 32 (FIG. 7) in a snap fit. Accordingly, the snapping portion includes one or more lever arms, prongs or tangs 370 (see FIG. 17A). Each lever arm 370 preferably includes a protrusion 372 that can be beveled or rounded (as illustrated). As mentioned above, the protrusions 372 are preferably sized and configured to snap into and resiliently engage the indentation 42 of the healing cap 10. Accordingly, the protrusions have an outer diameter D4 that is slightly larger than the diameter of the neck 44 of the corresponding indentation 42. Although two lever arms 370 with protrusions 372 thereon are illustrated, this number may be varied to produce the desired retention force and simplify manufacturing. For example, as few as one protrusions may be sufficient or six or more may alternatively be used.

The removal snapping portion 350 and healing cap 32 are preferably configured so that a force required to remove the healing cap 32 from the implant 10 is less than the force required to remove the snapping portion from the healing cap 32. Therefore, when the dentist lifts the insertion tool 340 away from the implant 10, the healing cap 32 remains attached to the tool 340 but detaches from the implant 10.

In contrast, the insertion snapping portion 348 is configured so that the force required to remove the healing cap 32 from the implant 10 is greater than the force required to remove the insertion snapping portion 348 from the healing cap 32. As with the removal portion 350, the insertion portion 348 is configured engage the indentation 42 on top of the healing cap 32 (FIG. 7) in a snap fit. The insertion portion 348 includes one or more lever arms, prongs or tangs 380. Each lever arm 380 preferably includes a protrusion 382 that can be beveled or rounded. Although two lever arms 380 with protrusions 382 thereon are illustrated, this number may be varied to produce the desired retention force and simplify manufacturing. For example, as few as one protrusions may be sufficient or six or more may alternatively be used. The protrusions 382 are preferably sized and configured to snap into and resiliently engage the indentation 42 of the healing cap 10. Accordingly, the protrusions have an outer diameter D7 that is slightly larger than the diameter of the neck 44 of the indentation 42. However, to reduce the force required to remove the insertion snapping portion 348 from the healing cap 32, the outer diameter D7 of the insertion snapping portion is preferably smaller than the outer diameter D4 diameter of the removal snapping portion 350. In addition, or instead of, the insertion snapping portion 348 can be made of a less resilient material as compared to the removal snapping portion 350 and/or the lever arms 380 can be thinner and/or for flexible than the lever arms 370 of the removal snapping portion 350.

Preferably, the insertion tool 340 includes indicia 390a, 390b to distinguish the insertion snapping portion 348 from the removal snapping portion 350. In the illustrated embodiment, the indicia 390a, 390b comprises a single groove on the handle 354 near the insertion snapping portion 348 and two grooves near the removal snapping portion 350. Of course, the indicia may be formed in a variety of other ways. For example, the letter "R" can be used to indicate the removal snapping prong 350 and/or the letter "I" can be used to indicated the insertion snapping prong 348. In other embodiments, the snapping portions 348, 350 can have different colors. In other embodiments, only one of the two snapping portions 348, 350 may include indicia.

In use, the insertion tool 340 can be used to insert the healing cap 32 into the dental implant 10 and to remove the healing cap 32 from the dental implant 10. To attach the healing cap 32 to the implant 10 during stage I, the surgeon first inserts the insertion snapping portion 348 into the indentation 42 of the healing cap 32. As such, the healing cap 32 is secured to the tool 340 and the dental practitioner can use the tool 340 to move the healing cap 32 into the patient's and to position the healing cap 32 over the dental implant 10. Once in position, the dental practitioner uses the tool 340 to push the snapping portion 50 of the healing cap 32 into the implant 10. As mentioned above, the insertion snapping portion 348 is configured so that the force required to remove the healing cap 32 from the implant 10 is greater than the force required to remove the insertion snapping portion 348 from the indentation 42. Thus, when the dentist lifts the insertion tool 340 away from the implant 10, the tool 340 detaches from the healing cap 32 and the healing cap 32 remains attached to the implant 10.

To remove the healing cap, the dental practitioner inserts the removal snapping portion 350 into the indentation 42 of the healing cap 32. As mentioned above, the handle removal snapping portion 350 and healing cap 32 are preferably configured so that the force required to remove the healing cap 32 from the implant 10 is less than the force required to remove removal snapping portion 350 from the healing cap 32. Therefore, when the dental practitioner lifts the tool 340 away from the implant 10, the healing cap 32 remains attached to the tool 340 and detaches from the implant 10.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications, combinations and sub-combinations and equivalents thereof. Thus, it is intended that the scope of the present invention herein disclosed should not be limited by the particular disclosed embodiments described above, but should be determined only by a fair reading of the claims that follow.

We claim:

1. A combination comprising a dental implant, a healing cap for covering a top surface of the implant and a tool for inserting and removing the healing cap;

the dental implant having a coronal opening;

the healing cap comprising a proximal end and a distal end, the proximal end being configured with one or more prongs adapted to be inserted into the coronal opening of the implant and to engage and secure the healing cap to the implant, the one or more prongs of the proximal end adapted such that a healing cap removal force is required to disengage the healing cap from the dental implant, the distal end of the healing cap including an indentation having a neck with a diameter smaller than a diameter of a lower portion of the indentation;

the insertion tool comprising a first portion with one or more prongs adapted to be inserted into the indentation, the first portion being adapted such that a first removal force is required to remove the one or more prongs of the first portion from the indentation, the first removal force being less than the healing cap removal force.

2. The combination as in claim 1, wherein the insertion tool includes a second portion with one or more prongs also adapted to be inserted into the indentation, the one or more prongs of the second portion being adapted such that a second removal force is required to remove the second portion from the indentation, the second removal force being greater than the healing cap removal force.

3. The combination of claim 2, wherein the one or more prongs of the first portion have a smaller diameter than the one or more prongs of the second portion.

4. The combination of claim 2, wherein the one or more prongs of the first portion are more flexible than the one or more prongs of the second portion.

5. The combination of claim 2, wherein the insertion tool includes indicia that distinguishes the first portion from the second portion.

6. The combination of claim 2, wherein the first portion of the insertion tool extends generally about a first axis and the second portion of the insertion tool extends generally about a second axis, the first axis and the second axis substantially lie within a single plane.

7. The combination of claim 6, wherein the first portion and the second portion extend in opposite directions.

8. The combination of claim 6, wherein the first axis and the second axis are generally perpendicular to a longitudinal axis of a handle of the insertion tool.

9. The combination of claim 2, wherein the first portion of the insertion tool extends generally about a first axis and the second portion of the insertion tool extends generally about a second axis, the insertion tool including a handle with at least one flat portion that defines a plane which lies generally traverse to either the first axis or the second axis.

10. The combination of claim 9, wherein the plane lies generally perpendicular to either the first axis or the second axis.

11. The combination of claim 9, wherein the first axis and the second axis substantially lie within a single plane.

12. The combination as in claim 1, further comprising a second insertion tool that includes a second portion with one or more prongs adapted to be inserted into the indentation, one or more prongs of the second portion being adapted such that a second removal force is required to remove the one or more prongs of the second portion from the indentation, the second removal force being greater than the healing cap removal force.

13. The combination of claim 12, wherein the one or more prongs of the first portion have a smaller diameter than the one or more prongs of the second portion.

14. The combination of claim 12, wherein the one or more prongs of the first portion are more flexible than the one or more prongs of the second portion.

15. A set of dental components comprising a dental implant, a healing cap for covering a top surface of the dental implant when installed in a patient's jawbone and an insertion tool, the healing cap comprising a first end adapted to be snappingly mated to the implant with a healing cap removal force and further comprising a second end adapted to completely cover the top surface of the implant, the insertion tool including a first portion to be snappingly mated to the second end of the healing cap with a first removal force, the first removal force being less than the healing cap removal.

16. The set as in claim 15, wherein insertion tool includes a second portion to be snappingly mated to the second end of the healing cap with a second removal force, the second removal force being greater than the healing cap removal force.

17. The set of claim 16, wherein the insertion tool includes indicia that distinguishes the first portion from the second portion.

18. The set of claim 16, wherein the first portion of the insertion tool extends generally about a first axis and the second portion of the insertion tool extends generally about a second axis, the first axis and the second axis substantially lie within a single plane.

19. The set of claim 18, wherein the first portion and the second portion extend in opposite directions.

20. The set of claim 18, wherein the first axis and the second axis are generally perpendicular to a longitudinal axis of a handle of the insertion tool.

21. The set of claim 16, wherein the first portion of the insertion tool extends generally about a first axis and the second portion of the insertion tool extends generally about a second axis, the insertion tool including a handle with at least one flat portion that defines a plane which lies generally traverse to either the first axis or the second axis.

22. The set of claim 21, wherein the plane lies generally perpendicular to either the first axis or the second axis.

23. The set of claim 21, wherein the first axis and the second axis substantially lie within a single plane.

24. The set as in claim 15, further comprising a second insertion tool that includes a second portion to be snappingly mated to the second end of the healing cap with a second removal force, the second removal force being greater than the healing cap removal force.

25. A method of installing and removing a healing cap that covers a top surface of an implant installed in a patient's jawbone, comprising in sequence:

engaging in a snap fit a first portion of an insertion tool with a top portion of the healing cap;

positioning the healing cap over a dental implant;

inserting a proximal end of the healing cap into a coronal opening of the implant until the proximal end engages the coronal opening in a snap fit so as to secure the healing cap to the implant; and separating the first portion of the insertion tool from the top portion of the healing cap.

26. The method of claim 25, further comprising engaging in a snap fit a second portion of the insertion tool with the top portion of the healing cap and separating the healing cap from the implant by moving the insertion tool away from the implant.

27. The method of claim 25, further comprising engaging in a snap fit a second portion of a second insertion tool with the top portion of the healing cap and separating the healing cap from the implant by moving the second insertion tool away from the implant.

* * * * *